United States Patent [19]

Del Rossi et al.

[11] Patent Number: 5,043,501
[45] Date of Patent: Aug. 27, 1991

[54] PROCESS FOR PREPARING DIMETHYLNAPHTHALENE

[75] Inventors: Kenneth J. Del Rossi, Mantua; Larry A. Green, Mickleton, both of N.J.; Albin Huss, Jr., Chadds Ford, Pa.; Garry W. Kirker, Washington Township, Gloucester County, N.J.; Michael E. Landis, Woodbury, N.J.

[73] Assignee: Mobil Oil Corp., Fairfax, Va.

[21] Appl. No.: 494,255

[22] Filed: Mar. 15, 1990

[51] Int. Cl.$^5$ .......................... C07C 2/00; C07C 2/64; C07C 5/22

[52] U.S. Cl. .................... 585/323; 585/411; 585/449; 585/467; 585/481; 585/482

[58] Field of Search ............... 585/323, 467, 411, 410, 585/480, 482, 449, 481

[56] References Cited

U.S. PATENT DOCUMENTS

| | | | |
|---|---|---|---|
| 3,775,496 | 11/1973 | Thompson | 260/668 F |
| 3,931,348 | 1/1976 | Taniguchi et al. | 585/411 |
| 4,439,409 | 3/1984 | Puppe et al. | 423/328 |
| 4,777,312 | 10/1988 | Bakas et al. | 585/481 |
| 4,795,847 | 1/1989 | Weitkamp et al. | 585/467 |
| 4,826,667 | 5/1989 | Zones et al. | 423/277 |
| 4,891,458 | 1/1990 | Innes et al. | 585/467 |

FOREIGN PATENT DOCUMENTS

| | | | |
|---|---|---|---|
| 0231860 | 8/1987 | European Pat. Off. | 502/64 |
| 0293032 | 11/1988 | European Pat. Off. | 502/73 |
| 3334084 | 4/1985 | Fed. Rep. of Germany | 585/467 |
| 2133032 | 7/1984 | United Kingdom | 585/467 |

Primary Examiner—Curtis R. Davis
Assistant Examiner—Nhat Phan
Attorney, Agent, or Firm—Alexander J. McKillop; Charles J. Speciale; Dennis P. Santini

[57] ABSTRACT

A process for producing 2,6-dimethylnaphthalene by alkylation of an alkylaromatic, e.g. toluene, with a $C_5$ olefin alkylating agent, e.g. 1-pentene, in the presence of a suitable alkylation catalyst, and dehydrocyclization of the resulting alkylate with a dehydrocyclization catalyst to generate a dimethylnaphthalene product rich in the 2,6-isomer. Additional process steps can include isomerization of the product and further alkylation.

20 Claims, 1 Drawing Sheet

PROCESS FOR PREPARING DIMETHYLNAPHTHALENE

CROSS-REFERENCE TO RELATED APPLICATIONS

This application is related by subject matter to U.S. Pat. application Ser No. 469,998, filed Jan. 25, 1990, and U.S. Pat. application Ser. No. 07/494,203, filed concurrently herewith.

BACKGROUND OF THE INVENTION

1. Field of the Invention

This invention relates to a process for preparing dimethylnaphthalene using a zeolite catalyst. Specifically it relates to a process for alkylating toluene and dehydrocyclizing the alkylate to produce a product rich in 2,6-dimethylnaphthalene.

2. Background of the Art

The compound 2,6-dimethyl naphthalene is a high valued commodity chemical that is used in the manufacture of polymers and polyester resins. Up to now, some of the methods for producing dimethylnaphthalene have required expensive starting materials such as 4-pentenyl-toluene; 5-(o-tolyl)-pent-2-ene; and 1,3-dimethyl-4-isobutylbenzene. These materials are cyclized, usually by means of a noble metal/alumina catalyst.

Dimethylnaphthalenes can also be produced by alkylating naphthalene and/or methylnaphthalene with methylating agent(s) in the presence of crystalline silicates with a moles ratio of $SiO_2/M_2O_3$ of 12 or more, wherein M is typically aluminum.

Isomerization using zeolite catalysts has also been employed.

For example, U.S. Pat. No. 4,777,312 (Bakas et al.) describes a method for isomerization of a feedstock of mixed dimethylnaphthalenes to produce a higher concentration of 2,6-dimethylnaphthalene isomer than in the feedstock. This method employs mordenite type zeolite as a catalyst.

U.S. Pat. No. 3,775,496 (Thompson) describes a multistep process for the preparation of 2,6-dimethylnaphthalene and 2,7-dimethylnaphthalene from 5-0-tolyl-pentene-2. The 5-0-tolyl-pentene-2 is first converted to a mixture of 1,6- and 1,8-dimethyltetralins, which are then dehydrogenated to the respective dimethylnaphthalenes. The dimethylnaphthalenes (DMN) are then isomerized respectively to 2,6-dimethylnaphthalene and 2,7-dimethylnaphthalene.

U.S. Pat. No. 4,795,847 (Weitkamp et al.) discloses a process for the preparation of 2,6-dialkylnaphthalenes by selectively alkylating naphthalene or 2-alkyl-naphthalene with an alkylating agent such as methanol in the presence of a zeolite ZSM-5 catalyst.

United Kingdom Patent No. GB 2,133,032 discloses a method for preparing dimethylnaphthalenes by reacting monomethyl naphthalene with methanol in the presence of an alumina, silica, or silica-alumina catalyst.

German Patent No. DE 3,334,084 mentions the use of ZSM-5 as a catalyst for the alkylation of naphthalene or alkylnaphthalene with methanol or dimethyl ether.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Alkylation is one of the most important and useful reactions of hydrocarbons. Lewis and Bronsted acids, including a variety of natural and synthetic zeolites, have been used as catalysts. Alkylation of aromatic hydrocarbon compounds employing certain crystalline zeolite catalysts is known in the art. For instance, U.S. Pat. No. 3,251,897 describes liquid phase alkylation in the presence of crystalline aluminosilicates such as faujasite, heulandite, clinoptilolite, mordenite, dachiardite, zeolite X and zeolite Y. The temperature of such alkylation procedure does not exceed 600° F., thereby maintaining patentee's preferable operating phase as substantially liquid.

Also, U.S. Pat. No. 2,904,607 shows alkylation of hydrocarbon compounds in the presence of certain crystalline zeolites. The zeolites described for use in this patent are crystalline metallic aluminosilicates, such as, for example, magnesium aluminosilicate.

U.S. Pat. Nos. 3,631,120 and 3,641,177 describe liquid phase processes for alkylation of aromatic hydrocarbons with olefins in the presence of certain zeolites. U.S. Pat. No. 3,631,120 discloses use of an ammonium exchanged, calcined zeolite having a silica to alumina mole ratio of between 4.0 and 4.9. U.S. Pat. No. 3,641,177 discloses use of a zeolite catalyst activated in a particular manner.

U.S. Pat. Nos. 3,751,504 and 3,751,506 describe the vapor phase alkylation of aromatic hydrocarbons with olefins in the presence of a specified type of zeolite catalyst.

U.S. Pat. Nos. 3,755,483 and 4,393,262 disclose the vapor phase reaction of propylene with benzene in the presence of zeolite ZSM-12, to produce isopropylbenzene.

U.S. Pat. No. 4,469,908 discloses the alkylation of aromatic hydrocarbons with relatively short chain alkylating agents having from one to five carbon atoms employing ZSM-12 as alkylation catalyst.

Harper et al. have described a catalytic alkylation of benzene with propylene over a crystalline zeolite (Petrochemical Preprints, American Chemical Society, Vol. 22, No. 3, p. 1084, 1977). Extensive kinetic and catalyst aging studies were conducted with a rare earth exchanged Y-type zeolite (REY) catalyst.

SUMMARY OF THE INVENTION

Provided herein is a method for making dimethylnaphthalene (DMN) in a two-step process. The first step involves alkylating an alkylaromatic feedstock with a $C_5$ olefin alkylating agent in the presence of a synthetic porous crystalline material having a Constraint Index of not greater than about 5, preferably not greater than about 3, a non-limiting example of which is characterized by an X-ray diffraction pattern including interplanar d-spacings at 12.36±0.4, 11.03 ±0.2, 8.83 ±0.14, 6.18 ±0.12, 6.00±0.10, 4.06±0.07, 3.91±0.07 and 3.42±0.06 Angstroms. AlkylatiOn conditions include a temperature of from about 0° F. to 900° F. and a pressure of from about 0.2 to about 250 atmospheres.

The resulting alkylate is then dehydrocyclized in the second step of the present process with a dehydrocyclization catalyst such as, for example, Pt/Ba/K/zeolite L to produce a product rich in dimethylnaphthalene. Dehydrocyclization conditions include a temperature of from about 500° F. to 1500° F., a pressure of from about 0 to about 1000 psig, a hydrogen to hydrocarbon molar ratio of from about 1 to about 10, and a liquid hourly space velocity (LHSV) of from about 0.1 to about 20 $hr^{-1}$.

Specifically, the process described herein can generate a product rich in 2,6-dimethylnaphthalene wherein the feedstock is toluene and the alkylating olefin is 1-pentene.

The product also can contain naphthalene, monomethylnaphthalene, and other isomers of dimethylnaphthalene. Optional additional processes can include isomerizing the dimethylnaphthalenes in the product to increase the fraction of the 2,6-isomer, and alkylating the naphthalene and monomethylnaphthalene with methanol in the presence of the above alkylation catalyst to produce dimethylnaphthalene, including the 2,6-isomer.

DETAILED DESCRIPTION OF THE PREFERRED EMBODIMENTS

Figure 1:
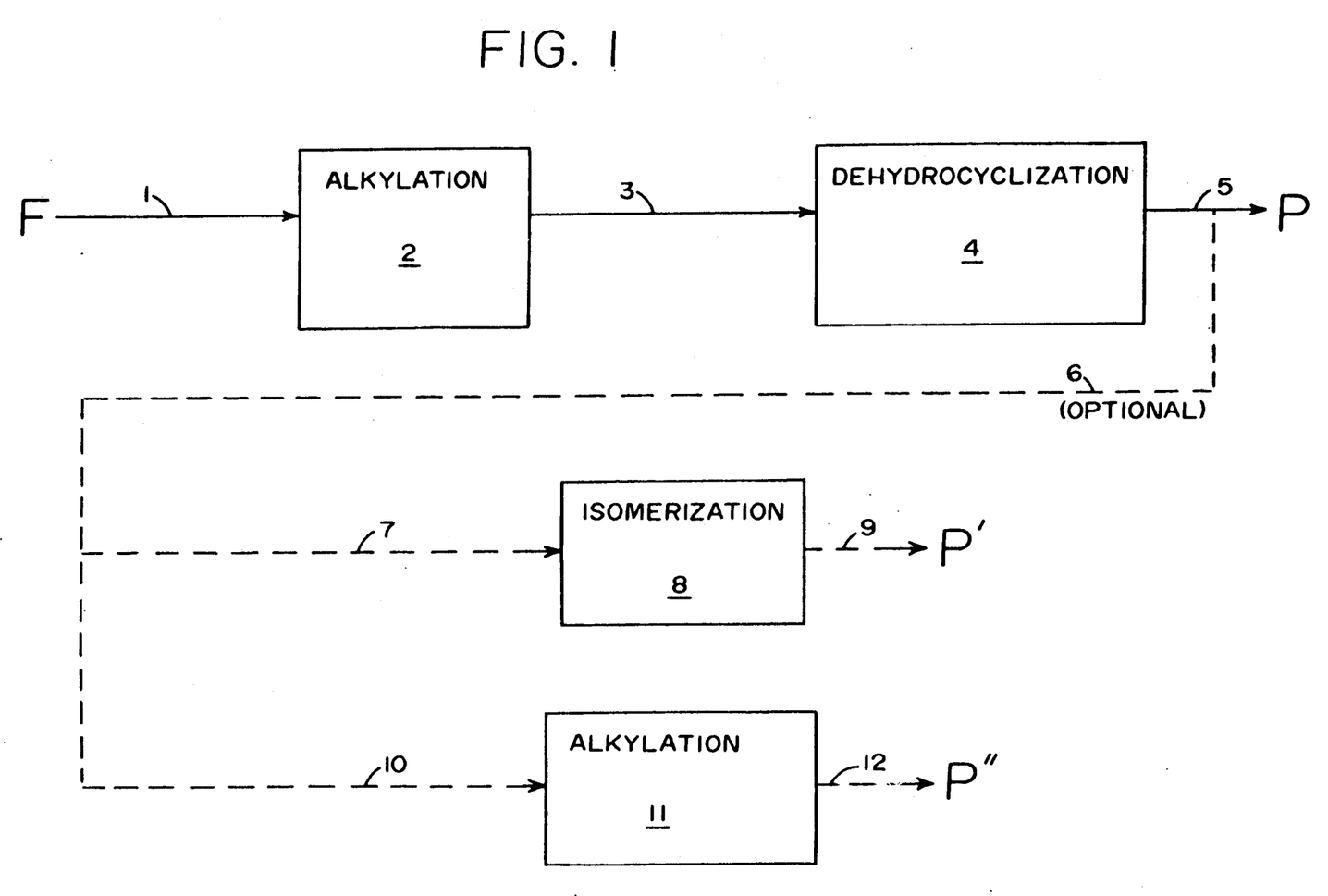
FIG. 1 is a flow chart of the process of the present invention.

The process of the present invention involves a two-step process. Referring to FIG. 1, a feedstock F comprising, for example, toluene and $C_5$ olefin, is introduced into alkylation reactor 2 via stream 1. Preferably the $C_5$ olefin is 1-pentene. Reactor 2 contains catalyst comprising a synthetic porous crystalline material having a Constraint Index of not greater than about 5, preferably not greater than about 3, an example of which is characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

The method by which Constraint Index is determined is described fully in U.S. Pat. No. 4,016,218, incorporated herein by reference for details of the method. Constraint Index (CI) values for some typical zeolites including some which are suitable as catalysts in the alkylation step of this invention are:

|  | CI (at test temperature) |
| --- | --- |
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those zeolites which are useful in the alkylation step of the present invention. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 5 or less, depending on the temperature employed during the test method within the range of 290° C. to about 538° C., with accompanying conversion between 10% and 60%, the CI may vary within the indicated range of 5 or less. Accordingly, it will be understood by those skilled in the art that the CI as utilized herein, while affording a highly useful means for characterizing the zeolites of interest, is approximate taking into consideration the manner of its determination including the possiblity in some instances of compounding variable extremes. However, in all instances, at a temperature within the above-specified range of 290° C. to about 538° C., the CI will have a value for any given zeolite of interest herein of not greater than about 5 and preferably not greater than about 3.

Some zeolite catalysts which are useful in the process of this invention include zeolites ZSM-4, ZSM-12, ZSM-20, ZSM-35, ZSM-48, ZSM-50, MCM-22, TMA offretite, TEA mordenite, clinoptilolite, mordenite, REY and zeolite Beta. Of these, zeolites ZSM-12, MCM-22 and Beta are preferred and zeolite MCM-22 is particularly preferred.

Zeolite ZSM-4 is taught in British Patent No. 1,117,568; ZSM-12 in U.S. Pat. No. 3,832,449; ZSM-20 in U.S. Pat. No. 3,972,983; ZSM-35 in U.S. Pat. No. 4,016,245; ZSM-48 in U.S. Pat. No. 4,397,827; ZSM-50 in U.S. Pat. No. 4,640,849; and Beta in U.S. Pat. No. 3,308,069, each incorporated herein by reference.

In its calcined form, another synthetic porous crystalline material component useful in the catalyst composition used in the process of this invention is characterized by an X-ray diffraction pattern including the following lines:

TABLE A

| Interplanar d-Spacing (A) | Relative Intensity, $I/I_o \times 100$ |
| --- | --- |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | M-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
| --- | --- |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

More specifically, it may be characterized in its calcined form by an X-ray diffraction pattern includng the following lines:

TABLE D

| Interplanar d-Spacing (A) | Relative Intensity $I/I_o \times 100$ |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiaiton was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interpalnar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

W=0–20
M=20–40
S=40–60
VS=60–100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g., silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

(0.005–0.1)$Na_2O$:(1–4)$R$:$X_2O_3$:$nYO_2$ wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400m$^2$/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Preferred cations are those which tailor the activity of the catalyst for alkylation. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A–D.

Prior to its use in the catalyst composition herein, the synthetic porous crystalline material zeolite should be subjected to thermal treatment to remove part or all of any organic constituent present therein.

The zeolite present in the catalyst composition herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the zeolite and/or matrix with which the zeolite may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing the platinum metal-containing ion. Thus, suitable platinum compounds for this purpose include chloroplatinic acid, platinous chloride and various compounds containing the platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal temperature can be performed at a temperature of up to about 925° C.

Prior to its use in the catalyst composition and process of this invention, the zeolite crystals should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the crystalline material in a vacuum but a longer time will be required to achieve a suitable degree of dehydration.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, or organic (R) directing agent, hereinafter more particularly described, and water, said reaction mixture having a composition, in terms of mole ratios of oxides, within the following ranges:

| Reactants | Useful | Preferred |
| --- | --- | --- |
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2O$ | .01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30. wt. % solid $YO_2$. Where YO is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration) favors MCM-22 crystal formation from the above mixture and is a distinct difference over the synthesis method disclosed in U.S. Pat. No. 4,459,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 material will vary with the nature of the reaction mixture employed and the crystallization conditions. In all cases, synthesis of the MCM-22 crystals is facilitated by the presence of at least about 0.01 percent, preferably about 0.10 percent and still more preferably about 1 percent, seed crystals based on the total weight of the crystalline product formed.

The zeolite crystals can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desirable to incorporate the zeolite crystalline material with another material, i.e., a binder, which is resistant to the temperatures and other conditions employed in the process of this invention. Suitable binder materials include active and inactive materials and synthetic or naturally occurring zeolite as well as inorganic materials such as clays, silica and/or metal oxides such as alumina. The latter can be either naturally occurring or provided in the form of gelatinous precipitates or gels including mixtures of silica and metal oxides. Use of a binder material in conjunction with the zeolite, i.e., combined therewith or present during its synthesis, which itself is catalytically active may change the conversion and/or selectivity of the catalyst. Inactive materials also serve as diluents to control the amount of conversion so that products can be obtained economically and in a controlled fashion without having to employ other means for controlling the rate of reaction.

These materials can be incorporated into naturally occurring clays, e.g., bentonite and kaolin, to improve the crush strength of the zeolite under commercial operating conditions. Good crush strength is an advantageous attribute for commercial use since it prevents or delays breaking down of the catalyst into powder-like materials.

Naturally occurring clays which can be composited with the zeolite crystals include the montmorillonite and kaolin family, which families include the subbentonites, and the kaolines commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

Apart from or in addition to the foregoing binder materials, the zeolite crystals can be composited with an organic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may also be advantageous to provide at least a part of the foregoing matrix materials in colloidal form so as to facilitate extrusion of the bound catalyst component(s).

The relative proportions of finely divided crystalline material and inorganic oxide matrix can vary widely with the zeolite content ranging from about 1 to about 95 percent by weight and more usually, particularly when the composite is prepared in the form of beads, in the range of about 2 to about 80 weight percent of the composite.

The stability of the zeolite for use as alkylation catalyst herein may be increased by steaming, with suitable stabilization conditions including contacting the catalyst with, for example, 5–100% steam at a temperature of at least 300° C. (e.g. 300°–650° C.) for at least one hour (e.g. 1–200 hours) at a pressure of 100–2,500 kPa. In a more particular embodiment, the catalyst can be made to undergo steaming with 75–100% steam at 315–500° C. and atmospheric pressure for 2–25 hours.

Alkylation of the alkylaromatic, e.g. toluene, in accordance with the first step of the invention is effected by contact of the reactants at a temperature of from about 0° F. to about 900° F., preferably from about 50° F. to about 500° F. The reaction generally takes place at pressures of from about 0.2 to about 250 atmospheres, preferably from about 1 to about 25 atmospheres. The molar ratio of alkylaromatic, e.g. toluene, to olefin alkylating agent, e.g. 1-pentene, can be from about 0.1:1 to about 50 : 1, preferably from about 0.5:1 to about 5:1. Reaction is suitably accomplished utilizing a feed weight hourly space velocity (WHSV) of from about 0.1 to about 500 hr$^{-1}$, preferably from about 0.5 to about 100 hr$^{-1}$. The WHSV is based upon the total weight of active catalyst (and binder if present).

The alkylation process step of this invention can be carried out as a batch-type, semi-continuous or continuous operation utilizing a fixed, fluidized or moving bed catalyst system. The product of the alkylation reaction of toluene with 1-pentene is drawn off via stream 3 and contains over 90% isoamyltoluene. Stream 3 is introduced into dehydrocyclization reactor 4 where it is contacted with a dehydrocyclization catalyst, such as Pt/Ba/K/zeolite L, under dehydrocyclization conditions.

Zeolite L is a large pore zeolite. Barium and potassium components of the catalyst increases its selectivity for dehydrocyclization reactions. More information regarding use of zeolite L in dehydrocyclization reactions may be found in U.S. Pat. No 4,650,565 (Jacobson et al.) and U.S. Pat. No. 4,746,764 (Lambert et al.), both of which are incorporated by reference herein.

Dehydrocyclization may be done at a temperature of about 500° F. to 1500° F., a pressure of from about 0 to 1000 psig, and a liquid hourly space velocity (LHSV) of about 0.1 to 20 hr$^{-1}$. Hydrogen may be employed as a diluent and may be circulated at a rate of from about 1 to 10 moles of hydrogen per mole of charge stock hydrocarbon.

The product P may be drawn off from the dehydrocyclization reactor 4 via stream 5, or, alternatively, all or a portion of effluent from dehydrocyclization reactor 4 may optionally be directed via stream 6 to an isomerization reactor 8 and/or to an alkylation reactor 11.

Effluent 5 contains dimethylnaphthalenes including the 2,6 isomer and other isomers, as well as naphthalene and monomethylnaphthalenes. The dimethylnaphthalene fraction 7 may be directed to the isomerization reactor 8 to enhance the concentration of the 2,6 isomer. A process for isomerization of dimethylnaphthalenes employing mordenite type zeolite catalyst is described in U.S. Pat. No. 4,777,312 (Bakas et al.), herein incorporated by reference. Specifically, the isomerization catalyst described therein comprises a hydrogen form mordenite dispersed in an alumina matrix and with a Group VIII noble metal (e.g. platinum, palladium, etc.) incorporated therein. The isomerization conditions include a temperature of from 300° C. to 450° C., a pressure of from about 1 to 20 atmospheres, a liquid hourly space velocity of from about 0.5 to 5 $hr^{-1}$, and a hydrogen to hydrocarbon molar feed ratio of from about 1 to about 7. A product P' enhanced in 2,6-dimethylnaphthalene can be drawn off via stream 9.

Other products from dehydrocyclization reactor 4 such as naphthalene and mono-methylnaphthalene may be directed via stream 10 to alkylation unit 11 where they may be reacted with methanol ($CH_3OH$) in the presence of alkylation catalyst, such as that used in reactor 2, at the conditions employed in reactor 2. A product P'' enhanced in 2,6-dimethylnaphthalene can be drawn off via stream 12.

In order to more fully illustrate the process of this invention and the manner of practicing same, the following examples are presented. In examples illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr cyclohexane vapor, pressure less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 $sec^{-1}$). The Alpha Test is described in U.S. Pat. 3,354,078; in the Journal of Catalysis, vol. 4, p. 527 (1965); vol. 6, p. 278 (1966); and vol. 61, p. 395 (1980), each incorporated herein by reference as to that description. The experimental conditions of the test used herein include a constant temperature of 538° C. and a variable flow rate as described in detail in the *Journal of Catalysis*, vol. 61, p. 395.

EXAMPLE 1

One part sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (90% $SiO_2$).

The reaction mixture had the following composition, in molar ratios:
$SiO_2/Al_2O_3 = 30.0$
$OH^-/SiO_2 = 0.18$
$H_2O/SiO_2 = 44.9$
$Na/SiO_2 = 0.18$
$R/SiO_2 = 0.35$
where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the zeolite was measured to be 494 $m_2/g$.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio | 21.10 |

TABLE E

| Degrees 2-Theta | Interplanar d-Spacing (A) | I/I° |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |

TABLE E-continued

| Degrees 2-Theta | Interplanar d-Spacing (A) | I/I° |
|---|---|---|
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainles steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| Example | 3 | 4 | 5 |
|---|---|---|---|
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2O/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution was added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table G. Surface area and adsorption analyses were on calcined product (538° C.).

TABLE G

| Product Composition (uncalcined) | |
|---|---|
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3g samples of the calcined material ion-exchanged 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions. Exchange Ions

| | Ionic Composition, wt. % | | |
|---|---|---|---|
| | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the zeolite where X in the general formula, suora, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in molar ratios:
$SiO_2/B_2O_3 = 6.1$
$OH^-/SiO_2 = 0.06$
$H_2O/SiO_2 = 19.0$ $K/SiO_2 = 0.06$
$R/SiO_2 = 0.30$
where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 240° C. and found to have the following sorption capacities:

| | |
|---|---|
| $H_2O$ | 11.7 wt. % |
| Cyclohexane | 7.5 wt. % |
| n-Hexane | 11.4 wt. % |

The surface area of the calcined crystalline material was measured (BET) to be 405 m²/g.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio | 1406 |
| $SiO_2/(Al + B)_2O_3$, molar ratio | 25.8 |

EXAMPLE 12

A portion of the calcined crystalline product of Example 11 was treated with $NH_4Cl$ and again calcined. The final crystalline product was tested in the Alpha test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in molar ratios:
$SiO_2/B_2O_3 = 12.3$
$OH^-/SiO_2 = 0.056$
$H_2O/SiO_2 = 18.6$
$K/SiO_2 = 0.056$
$R/SiO_2 = 0.30$
where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ | 14.4 wt. % |
| Cyclohexane | 4.6 wt. % |
| n-Hexane | 14.0 wt. % |

The surface area of the calcined crystalline material was measured to be 438m²/g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al + B)_2O_3$, molar ratio | 28.2 |

EXAMPLE 14

A portion of the calcined crystalline product of Example 13 was tested in the Alpha Test and found to have an Alpha Value of 5.

EXAMPLE 15

In another example of zeolite synthesis, one part sodium aluminate (43.5% $Al_2O_3$, 33.3% $Na_2O$, 24.2% $H_2O$) dissolved in 0.7 parts water was added to a solution containing 1 part of 50% NaOH solution and 43.5 parts $H_2O$. Next was added 4.50 parts hexamethyleneimine. Ultrasil, a precipitated, spray-dried silica (90% $SiO_2$) was next added in the amount of 8.55 parts with stirring.

The reaction mixture had the following composition, in molar ratios:
$SiO_2/Al_2O_3 = 30.0$
$OH^-/SiO_2 = 0.18$
$H_2O/SiO_2 = 19.3$
$Na/SiO_2 = 0.18$
$R/SiO_2 = 0.35$
where R is hexamethyleneimine.

The mixture was crystallized in a stainless steel reactor, with stirring, at 143° C. for 3 days. The crystalline product was filtered, washed with water and dried at 120° C. A portion was calcined in $N_2$ at 538° C. for three hours, exchanged twice with ammonium nitrate (5 vol. 1.0N $NH_4NO_3$/vol cat.), washed nitrate free with deionized water, dried for 16 hours at 120° C. and air calcined for 3 hours at 538° C. The X-ray diffraction pattern contained the major lines listed in Tables A-D.

EXAMPLE 16

As a first step to the present process, alkylation of 600 grams of a mixture of two parts toluene/one part 1-pentene was carried out in a one liter stirred autoclave using 10.0 grams synthetic zeolite product of Example 15. The autoclave was heated to 300° F. and held at this temperature for 18 hours. The autoclave was then cooled to room temperature and the product analyzed by gas chromatography and mass spectrometry. The analyses showed that the alkylation of toluene was complete and resulted in the selective alkylation of toluene to an alkylate product containing over 90% isoamyltoluene. The autoclave product was distilled to remove the unreacted components.

EXAMPLE 17

A dehydrocyclization catalyst for use in the second step of the process was prepared in accordance with the following procedure:

Commercial zeolite L was calcined for 3 hours at 1000° F. in 3 vol/vol/minute nitrogen gas. The zeolite was then exchanged with barium ions ($Ba^{+2}$) for 3 hours at 176° F. and pH of 10. The zeolite was then filtered, washed, and dried at 250° F. overnight. The zeolite was then calcined for 3 hours at 1000° F. in 3 vol/vol/min air.

The above steps were repeated, and the zeolite was then impregnated with a 0.075 M solution of Pt (NH$_3$)$_4$Cl$_2$ using rotary-evaporator/incipient wetness techniques under a carbon dioxide atmosphere. The zeolite was then rolled for one hour under carbon dioxide atmosphere, dried, and then heated at 2° F./minute to 500° F., and calcined for 2 hours at 500° F. in 5 vol/vol/minute of air.

The resulting crystalline product was a Pt/Ba/K-/Zeolite L containing 0.87 wt. % platinum.

EXAMPLE 18

As the second step of the present process, the isoamyltoluene-containing product from Example 16 was reacted under dehydrocyclization conditions with the Pt/Ba/K/zeolite L catalyst produced in Example 17.

The dehydrocyclization reaction was performed in a fixed bed pilot unit equipped with a downflow ½ inch ID stainless steel reactor. The top portion of the reactor was packed with 5 cc of commercially available sulfur guard (HRD-264), and the lower portion was packed with 10 cc of 14/24 mesh Pt/Ba/K/zeolite L. The sulfur guard was pretreated in hydrogen at 500° C. for 4 hours prior to loading. The catalyst bed was heated at a rate of 220° F./hour in 100 cc/min of flowing hydrogen to 905° F., and then held at this temperature for one hour. Performance of the dehydrocyclization catalyst was initially tested with a n-hexane feed at 905° F., 100 psig, 3 WHSV, and 3:1 H$_2$/HC. The observed aromatics selectivity and C$_6$ paraffin conversion (Table H) were comparable to values reported in the patent literature. After catalyst performance was confirmed, the n-hexane feed was removed and replaced with the alkylate product from Example 16 (>90% isoamyltoluene). Liquid and gaseous products from the reaction were collected and analyzed on a non-polar capillary column. The data are given in Table H. Selectivities for naphthalenes and dimethylnaphthalenes were 15.6% and 5.6%, respectively.

The data given in Table H show that the process disclosed herein can generate dimethylnaphthalenes directly from low cost starting materials.

TABLE H

| Dehydrocyclization of Alkylates | Test Run | Process Step |
|---|---|---|
| Conditions | | |
| Pressure (psig) | 100 | 100 |
| Temperature (°F.) | 905 | 905 |
| H$_2$/HC molar ratio | 3 | 3 |
| Feed | n-hexane | Example 16 Product* |
| WHSV (hr$^{-1}$) | 3.2 | 1.1 |
| Product Distribution, wt. % | | |
| C$_5$- | 19.8 | 45.3 |
| Total Aromatics | 36.3 | 54.3 |
| Naphthalenes (Naph) | 0 | 8.4 |
| Dimethylnaphthalenes (DMN) | 0 | 2.7 |
| Aromatics Selectivity$ | 64.7 | 54.5 |
| Naph Selectivity& | 0 | 15.6 |
| DMN Selectivity# | 0 | 5.6 |

*Contains >90 wt % isoamyltoluene
$Defined as [(Aromatics/Aromatics +C5-) × 100]
&Defined as [(Naph/Naph + C5-) × 100]
Defined as [(DMN/DMN + C5-) × 100]

What is claimed is:

1. A process for producing dimethylnapthalene from a feedstock containing an alkylatable aromatic compound and a C$_5$ olefin, said process comprising:

a) contacting said feedstock with a first alkylation catalyst composition under alkylation conditions to produce an alkylate, said first alkylation catalyst composition comprising a synthetic crystalline material characterized by an X-ray diffraction pattern including interplanar d-spacings as set forth in Table A of the specification, and b) contacting said alkylate with a dehydrocyclization catalyst under dehydrocyclization conditions to produce a product containing dimethylnaphthalene.

2. The process of claim 1 wherein said crystalline material of said alkylation catalyst composition has a Constraint Index of not greater than about 3.

3. The process of claim 1 wherein the crystalline material of said first alkylation catalyst composition is characterized by an X-ray diffraction pattern including interplanar d-spacings as set forth in Table B of the specification.

4. The process of claim 1 wherein the crystalline material of said first alkylation catalyst composition is characterized by an X-ray diffraction pattern including interplanar d-spacings as set forth in Table C of the specification.

5. The process of claim 1 wherein the crystalline material of said first alkylation catalyst composition is characterized by an X-ray diffraction pattern including interplanar d-spacings as set forth in Table D of the specification.

6. The process of claim 1 wherein the synthetic crystalline material of said first alkylation catalyst has a composition comprising the molar relationship:

$$X_2O_3:(n)YO_2$$

wherein X is a trivalent element selected from the group consisting of aluminum, boron, iron and gallium, Y is a tetravalent element selected from the group consisting of silicon and germanium, and n is at least about 10.

7. The process of claim 1 wherein said first alkylation catalyst and dehydrocyclization catalyst have been treated to replace original ions, at least in part, with an ion or mixture of ions selected from the group consisting of hydrogen, rare earth metals, and metals of Groups IIA, IIIA, IVA, IB, IIB, IIIB, IVB, VIB and VIII of the Periodic Table.

8. The process of claim 1 wherein said catalysts have thermally treated at a temperature of up to about 925° C.

9. The process of claim 1 wherein the alkylatable aromatic compound in the feedstock is toluene.

10. The process of claim 1 wherein the C$_5$ olefin is 1-pentene.

11. The process of claim 1 wherein the alkylate contains isoamyltoluene.

12. The process of claim 1 wherein the dehydrocyclization catalyst comprises zeolite L.

13. The process of claim 1 wherein the alkylation conditions include a temperature of from about 0° F. to about 900° F. and a pressure of from about 0.2 atmosphere to about 250 atmospheres.

14. The process of claim 1 wherein the dehydrocyclization conditions include a temperature of from about 500° F. to about 1500° F. and a pressure of from about 0 to 1000 psig.

15. The process of claim 1 wherein the product of the dehydrocyclization step is contacted with an isomerization catalyst under isomerization conditions.

16. The process of claim 15 wherein said isomerization catalyst comprises a hydrogen form mordenite dispersed in an alumina matrix and with a Group VIII metal incorporated therein.

17. The process of claim 15 wherein the isomerization conditions include a temperature of from 550° F. to 850° F., a pressure of from about 1 to 20 atmospheres, a liquid hourly space velocity of from about 0.5 to 5 hr$^{-1}$, and a hydrogen to hydrocarbon molar feed ratio of from about 1 to 7.

18. The process of claim 1 wherein the product of the dehydrocyclization step is contacted under alkylation conditions with a methanol alkylating agent in the presence of a second alkylation catalyst comprising a synthetic crystalline material having a Constraint Index of not greater than about 5.

19. The process of claim 18 wherein the second alkylation catalyst comprises a synthetic crystalline material having the structure of one selected from the group consisting of ZSM-4, ZSM-12, ZSM-20, ZSM-35, ZSM-48, ZSM-50, MCM-22, TMA offretite, mordenite, clinoptilolite, zeolite Y and zeolite Beta.

20. A process for producing 2,6-dimethylnaphthalene from a feedstock containing toluene and I-pentene, said process comprising:
a) contacting said feedstock with an alkylation catalyst composition under alkylation conditions to produce an alkylate containing isoamyltoluene, said catalyst composition comprising a synthetic crystalline material characterized by an X-ray diffraction pattern including interplanar d-spacings as set forth in Table A of the specification and having a Constraint Index of not greater than about 5, and
b) contacting said alkylate with a dehydrocyclization catalyst under dehydrocyclization conditions to produce a product containing 2,6-dimethylnaphthalene.

* * * * *